United States Patent [19]
Terren et al.

[11] Patent Number: 6,159,486
[45] Date of Patent: Dec. 12, 2000

[54] WATER-IN-OIL EMULSION, COMPOSITION CONTAINING THE EMULSION AND USE THEREOF

[75] Inventors: Nadia Terren, Chevilly Larue, France; Jacqueline Fontaine, La Celle Saint Cloud, France

[73] Assignee: L'Oreal, Paris, France

[21] Appl. No.: 09/318,730

[22] Filed: May 26, 1999

Related U.S. Application Data

[62] Division of application No. 09/013,268, Jan. 26, 1998, Pat. No. 5,955,003.

[30] Foreign Application Priority Data

Jan. 24, 1997 [FR] France ................................. 97 00914

[51] Int. Cl.$^7$ ............................... A61K 7/00; A61K 7/42; A61K 7/021; A61K 7/025; A61K 7/06
[52] U.S. Cl. ............................ 424/401; 424/59; 424/63; 424/64; 424/70.1; 424/70.7; 424/70.11; 514/844; 514/937
[58] Field of Search ............................... 424/401, 59, 63, 424/64, 70.1, 70.7, 70.11; 514/844, 937

[56] References Cited

U.S. PATENT DOCUMENTS

| | | |
|---|---|---|
| 4,282,203 | 8/1981 | Jacquet et al. . |
| 4,871,536 | 10/1989 | Arraudeau et al. .................. 424/59 |
| 5,194,260 | 3/1993 | Grollier et al. ..................... 424/401 |
| 5,238,678 | 8/1993 | Shiozawa et al. . |
| 5,589,177 | 12/1996 | Herb et al. . |
| 5,620,693 | 4/1997 | Piot et al. . |
| 5,660,820 | 8/1997 | Mondet et al. . |
| 5,683,681 | 11/1997 | Ramin et al. . |
| 5,709,850 | 1/1998 | Mondet et al. . |
| 5,753,215 | 5/1998 | Mougin et al. ..................... 424/70.11 |
| 5,876,704 | 3/1999 | Collin et al. ........................ 424/63 |
| 5,925,337 | 7/1999 | Arraudeau et al. ................. 424/63 |

FOREIGN PATENT DOCUMENTS

| | | |
|---|---|---|
| 0 391 274 | 10/1990 | European Pat. Off. . |
| 0 655 234 | 5/1995 | European Pat. Off. . |
| 2 439 798 | 5/1980 | France . |
| 2 679 769 | 2/1993 | France . |
| 2 144 133 | 2/1985 | United Kingdom . |
| WO 95/03778 | 2/1995 | WIPO . |
| WO 96/33689 | 10/1996 | WIPO . |

*Primary Examiner*—Shelley A. Dodson
*Assistant Examiner*—Marina Lamm
*Attorney, Agent, or Firm*—Finnegan, Henderson, Farabow, Garrett & Dunner, L.L.P.

[57] ABSTRACT

A water-in-oil emulsion comprising a fatty phase comprising a an oil selected from volatile oils and, preferably, poly(C1–C20)-alkylsiloxanes and an aqueous phase comprising a dispersed film-forming polymer, and a cosmetic composition including the water-in-oil emulsion, preferably a compostion which transfers and/or migrates little.

10 Claims, No Drawings

WATER-IN-OIL EMULSION, COMPOSITION CONTAINING THE EMULSION AND USE THEREOF

This is a division of application Ser. No. 09/013,268, filed Jan. 26, 1998 now U.S. Pat. No. 5,955,003 which is incorporated herein by reference.

The invention relates to a water-in-oil emulsion comprising a polymer dispersed in the aqueous phase, and to its use in cosmetic, pharmaceutical and hygiene products.

Foundation compositions are generally in the form of a relatively fluid cream comprising fatty substances such as oils and a particulate phase generally composed of fillers and pigments. However, when these compositions are applied to the skin, they have the drawback of transferring, that is to say of being deposited, at least partly, leaving a trace on certain supports with which they may come into contact, and especially clothing or the skin. This results in mediocre persistence of the film on the skin, thereby making it necessary to repeat the application of the foundation composition regularly.

Another drawback of the compositions of the prior art lies in the problem of migration of these compositions, that is to say in the fact that the composition has a tendency to travel inside the folds and/or wrinkles of the face, giving an unaesthetic effect.

A foundation composition in water-in-oil emulsion form is known according to PCT patent application WO-A-96/33689, the fatty phase comprising volatile oils and a film-forming polymer being dispersed in the aqueous phase. Acrylic resins such as DERMACRYL LT are mentioned among the polymers recommended for use in this composition.

However, it has been observed that the addition of such a polymer to the aqueous phase has the drawback of destabilizing the emulsion over time. This is because, after storage, the emulsion does not retain its uniformity and it demixes rapidly, this being detrimental in terms of the properties required for the composition.

The aim of the present invention is to provide a water-in-oil emulsion which has good stability, while at the same time retaining good cosmetic properties. In particular, it is sought to make available a stable water-in-oil emulsion which does not transfer after it has been applied, especially onto the skin.

The inventors have discovered, surprisingly and unexpectedly, that by using a particular polymer dispersed in the aqueous phase of the emulsion, in combination with a particular choice of oils, a water-in-oil emulsion having said characteristics and also having the advantage of not transferring and of being stable can be obtained.

A subject of the present invention is thus a water-in-oil emulsion comprising a fatty phase comprising at least one volatile oil, and an aqueous phase comprising at least one a film-forming polymer dispersed in the aqueous phase, wherein the film-forming polymer is a copolymer comprising at least one carboxylic acid monomer residue containing at least one ethylenic unsaturation and at least one carboxylic acid ester monomer residue in which the group attached to the oxygen atom of the ester function contains at least one ethylenic unsaturation.

Another subject of the invention relates to a composition, in particular a cosmetic, pharmaceutical or hygiene composition, comprising an emulsion as defined above.

The invention also relates to a non-therapeutic process for treating the skin and/or the scalp, especially a make-up process, comprising applying to the skin and/or the scalp an emulsion and/or a composition as defined above.

Another subject of the invention relates to the use of the polymer dispersed in the aqueous phase of the water-in-oil emulsion in a so-called "transfer-free" composition, and/or in order to decrease the transfer and/or migration of a composition comprising it, on the skin.

It has also been observed that the emulsion used according to the invention applies and spreads easily and uniformly, without giving a greasy feel, and has good cosmetic properties. The film obtained also has a light texture and remains comfortable to wear throughout the day.

Furthermore, the emulsion applied to the skin has the advantage of not migrating in the folds of the skin and/or the wrinkles of the face.

Moreover, it is possible to add to the emulsion according to the invention other additives such as oils and/or powders (pigments and/or fillers) while at the same time retaining a stable emulsion. The emulsion is thus compatible with a large number of cosmetic adjuvants.

Lastly, it has been observed that the viscosity of the emulsion is stable over time.

Thus, according to the invention, at least one film-forming polymer dispersed in the aqueous phase of the emulsion is a copolymer comprising at least one carboxylic acid monomer residue containing at least one ethylenic unsaturation and at least one carboxylic acid ester monomer residue in which the group attached to the oxygen atom of the ester function contains at least one ethylenic unsaturation.

According to a different embodiment of the invention, the film-forming polymer can also comprise at least one carboxylic acid acrylate ester monomer residue wherein the at least one carboxylic acid acrylate ester monomer residue is not a carboxylic acid ester monomer residue in which the group attached to the oxygen atom of the ester function contains at least one ethylenic unsaturation.

Advantageously, the film-forming polymer dispersed in the aqueous phase can be selected from:

copolymers comprising at least one carboxylic acid monomer residue containing at least one ethylenic unsaturation and at least one carboxylic acid ester monomer residue in which the group attached to the oxygen atom of the ester function contains at least one ethylenic unsaturation, and copolymers comprising at least one carboxylic acid monomer residue containing at least one ethylenic unsaturation, at least one carboxylic acid ester monomer residue in which the group attached to the oxygen atom of the ester function contains at least one ethylenic unsaturation, and at least one carboxylic acid acrylate ester monomer residue, wherein the at least one carboxylic acid acrylate ester monomer residue is not a carboxylic acid ester monomer residue in which the group attached to the oxygen atom of the ester function contains at least one ethylenic unsaturation.

Among the radical film-forming polymers containing carboxylic acid functions which can be used according to the invention, mention may be made in particular of:

the vinyl acetate/crotonic acid copolymer (90/10) sold by the company BASF under the name "LUVISET CA66", and the vinyl acetate/crotonic acid/vinyl neodecanoate terpolymer sold by the company National Starch under the name "RESIN 28-29-30".

It is also possible to use, according to the invention, film-forming polymers having the general formula (I) below:

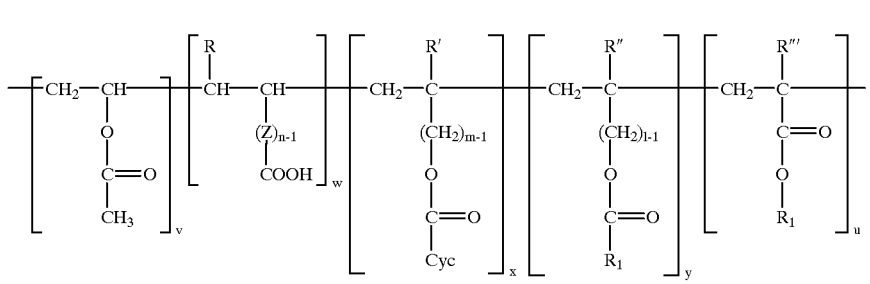

(I)

in which:
R, R', R" and R'" independently represent a hydrogen atom or a methyl radical,
m, n and t independently represent 1 or 2,
$R_1$ independently represents a linear or branched, saturated or unsaturated alkyl radical having from 2 to 21 carbon atoms,
Z represents a divalent radical selected from:

—$CH_2$—, —$CH_2$—O—$CH_2$— and —$CH_2$—O—$(CH_2)_2$—,

Cyc represents a radical selected from:

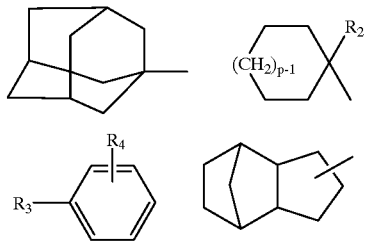

in which
$R_2$ represents a hydrogen atom or a methyl radical,
$R_3$ represents a hydrogen atom or a methyl, ethyl, tert-butyl, ethoxy, butoxy or dodecyloxy radical,
$R_4$ represents a hydrogen atom, an alkyl radical containing from 1 to 4 carbon atoms or an alkoxy radical containing from 1 to 4 carbon atoms,
p is equal to 1 or 2, and further in formula (I):
v preferably represents from 10 to 97% by weight, and more preferably from 36 to 84% by weight,
w preferably represents from 3 to 20% by weight, and more preferably from 6 to 12% by weight,
x preferably represents from 0 to 60% by weight, more preferably from 4 to 60%, and even more preferably from 6 to 40% by weight,
y preferably represents from 0 to 40% by weight, and more preferably from 4 to 30% by weight, and
u preferably represents from 0 to 30% by weight, and more preferably from 0 to 20% by weight, wherein v+w+x+y+u are equal to 100%.

Film-forming polymers of formula (I) are described in U.S. Pat. No. 4,282,203, the disclosures of which are specifically incorporated by reference herein.

The film-forming polymer can be dispersed in the aqueous phase of the emulsion according to the invention by simple addition of a latex or a pseudolatex of the film-forming polymer to the other ingredients of the aqueous phase of the emulsion, especially during the preparation of the emulsion.

The latices result directly from the synthesis of a polymer by a well-known technique of emulsion polymerization. The optional neutralization of the latex is such that the polymer remains in latex form and does not dissolve in the water.

In order to obtain a pseudolatex, a polymer is prepared and is then dispersed in the water. The dispersion in water is self-stabilized by at least partial neutralization of the acid groups carried by the polymer.

Aqueous dispersions in the form of a pseudolatex of the film-forming polymers mentioned above, and especially of the polymers of formula (I), are described in European patent applications U.S. Pat. Nos. 5,660,820 and 5,709,850, U.S. Pat. No. 5,753,215 and U.S. Pat. No. 5,683,681, the disclosures of which are specifically incorporated by reference herein.

More preferably, the vinyl acetate/crotonic acid/vinyl 4-tert-butylbenzoate copolymer (65/10/25) is used.

Advantageously, the carboxylic acid functions of the film-forming polymers are at least partially neutralized in order to obtain good dispersion of the film-forming polymer in the aqueous medium.

The degree of neutralization of the film-forming polymers containing carboxylic acid functions must be determined such that they remain insoluble in the water while at the same time being soluble in the organic solvent. Thus, the degree of neutralization must be less than 100%.

The lower and upper limit degrees of neutralization which should not be exceeded in order for the polymer to remain water-insoluble depend on the nature of each polymer and can readily be determined by a person skilled in the art on the basis of his or her general technical knowledge.

In general, the degree of neutralization ranges from 30 to 80% if the polymer has less than 2 meq/g of carboxylic acid functions, and from 10 to 50% if the polymer has more than 2 meq/g of carboxylic acid functions.

The carboxylic acid functions can be neutralized using a basic compound, such as an inorganic base, for instance sodium hydroxide or potassium hydroxide, or an amino-alcohol selected for example from 2-amino-2-methyl-1-propanol (AMP), triethanolamine, triisopropanolamine (TIPA), monoethanolamine, diethanolamine, tris[2-hydroxy-1-propyl]amine, 2-amino-2-methyl-1,3-propanediol (AMPD) and 2-amino-2-hydroxymethyl-1,3-propanediol. Lysine, arginine or cystine can also be used as neutralizing agents.

The average size of the film-forming polymer particles generally ranges from 10 to 300 nm, more preferably less than 250 nm, with a relatively low particle size polydispersity.

In order to obtain good film-forming properties of the polymer dispersed in the aqueous phase of the emulsion according to the invention, it may be advantageous to add at least one plasticizer with the film-forming polymer. This plasticizer can be hydrophilic or hydrophobic. It is selected so as to afford, in combination with the polymer considered, a flexible and non-brittle film. The plasticizer can be introduced as a mixture in the organic solvent, during the preparation of the aqueous dispersion, especially when it is of the hydrophobic type. When it is of the hydrophilic type, it can be introduced directly into the dispersion after it has been formed.

Among the plasticizers which can be used in the present invention, mention may be made of:

the CARBITOLS from the company Union Carbide, namely CARBITOL or diethylene glycol ethyl ether, methyl CARBITOL or diethylene glycol methyl ether, butyl CARBITOL or diethylene glycol butyl ether or hexyl CARBITOL or diethylene glycol hexyl ether, the CELLOSOLVES from the company Union Carbide, namely CELLOSOLVE or ethylene glycol ethyl ether, butyl CELLOSOLVE or ethylene glycol butyl ether, and hexyl CELLOSOLVE or ethylene glycol hexyl ether, propylene glycol derivatives and in particular propylene glycol phenyl ether, propylene glycol diacetate, dipropylene glycol butyl ether and tripropylene glycol butyl ether, as well as the DOWANOLS from the company Dow Chemical such as DOWANOL PM or propylene glycol methyl ether, DOWANOL DPM or dipropylene glycol ethyl ether, DOWANOL TPM or tripropylene glycol methyl ether and DOWANOL DM or diethylene glycol methyl ether, benzyl alcohol, triethyl citrate, 1,3-butylene glycol, diethyl, dibutyl and diisopropyl phthalates and adipates, diethyl and dibutyl tartrates, diethyl, dibutyl and bis(2-ethyl)hexyl phosphates, and glycerol esters such as glyceryl diacetate (diacetin) and glyceryl triacetate (triacetin).

From 5 to 60% of plasticizer is generally introduced relative to the weight of neutralized film-forming polymer solids, the plasticizing agent being distributed according to its partition coefficient between the particles and the aqueous phase.

According to the invention, the film-forming polymer dispersed in the aqueous phase of the emulsion can be present in a content preferably ranging from 0.3% to 10% by weight, and more preferably from 2% to 5%, relative to the total weight of the emulsion.

Advantageously, the emulsion according to the invention is prepared using an emulsifying surfactant which is suitable for the preparation of a stable water-in-oil emulsion, that is to say one having an HLB which makes it possible to obtain a water-in-oil emulsion. For example, the surfactant can be a silicone surfactant, and especially an oxyalkylenated silicone.

According to the invention, the term oxyalkylenated silicone refers to any silicone containing at least one oxyalkylenated group of ($-C_xH_{2x}O$) a type in which x can range from 2 to 6 and a is greater than or equal to 1.

Hereinabove and hereinbelow, in accordance with the definition generally accepted, the term silicone is understood to denote any organosilicon polymer or oligomer having a linear or cyclic, branched or crosslinked structure, of variable molecular weight, obtained by polymerization and/or polycondensation of suitably functionalized silanes and comprising a repetition of main units in which the silicon atoms are connected together by oxygen atoms (siloxane bond $\equiv$Si—O—Si$\equiv$), optionally substituted hydrocarbon radicals being attached directly via a carbon atom onto the silicon atoms. The most common hydrocarbon radicals are alkyl radicals, especially C1–C10 alkyl radicals and in particular methyl, fluoroalkyl radicals, and aryl radicals and in particular phenyl.

The oxyalkylenated silicones are selected, for example, from the compounds of general formulae (VII), (VIII), (IX) and (X):

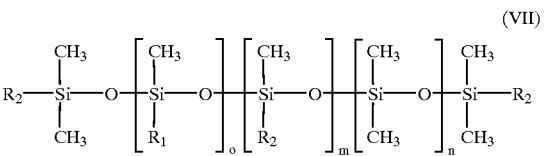

(VII)

(VIII)

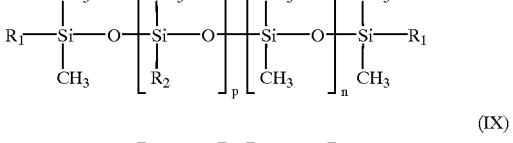

(IX)

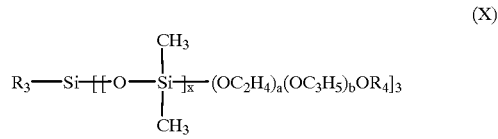

(X)

in which formulae:

$R_1$ independently represents a linear or branched C1–C30 alkyl or a phenyl radical, $R_2$ independently represents a radical —$C_cH_{2c}$—O—$(C_2H_4O)_a(C_3H_6O)_b$—$R_5$ or a radical —$C_cH_{2c}$—O—$(C_4H_8O)_a$—$R_5$, $R_3$ and $R_4$ independently denote a linear or branched C1–C12 alkyl radical and preferably a methyl radical, $R_5$ in the definition of $R_2$ independently represents a hydrogen atom, a linear or branched alkyl radical containing from 1 to 12 carbon atoms, a linear or branched acyl radical containing from 2 to 12 carbon atoms, a hydroxyl radical, a radical —$SO_3M$ or —$OCOR_6$, a C1–C6 aminoalkoxy radical optionally substituted on the amine, a C2–C6 aminoacyl radical optionally substituted on the amine, a radical —$NHCH_2CH_2COOM$ or —$N(CH_2CH_2COOM)_2$, an aminoalkyl radical optionally substituted on the amine and on the alkyl chain, a C2–C30 carboxyacyl radical, a phosphono group optionally substituted with one or two substituted aminoalkyl radicals, or a radical —CO$(CH_2)_dCOOM$, —$OCOCHR_7(CH_2)_dCOOM$, —NHCO$(CH_2)_dOH$ or —$NH_3Z$, in which M independently denotes a hydrogen, Na, K or Li atom, $NH_4$ or an organic amine, $R_6$ denotes a linear or branched C1–C30 alkyl radical, $R_7$ denotes a hydrogen atom or a radical $SO_3M$, d ranges from 1 to 10, m ranges from 0 to 20, n ranges from 0 to 500, o ranges from 0 to 20,
p ranges from 1 to 50,
a ranges from 0 to 50,
b ranges from 0 to 50,
wherein a+b is greater than or equal to 1,
c, in the definition of $R_2$, ranges from 0 to 4,
x ranges from 1 to 100,
Z, in the definition of $R_5$, represents an inorganic or organic monovalent anion such as halide (chloride, bromide), sulphate or carboxylate (acetate, lactate, citrate).

Oxyalkylenated silicones corresponding to the general formula (VII) or (VIII) are preferably used. More particularly, these formulae satisfy at least one, and preferably all, of the following conditions:
c is equal to 2 or 3,
$R_1$ independently denotes a methyl radical,
$R_5$ represents a hydrogen atom, a methyl radical or an acetyl radical and preferably a hydrogen atom,
a ranges from 1 to 25, and more particularly from 2 to 15,
b is equal to 0,
n ranges from 0 to 100,
p ranges from 1 to 20.

It is also possible to use oxyalkylenated silicones of formula (XI) below:

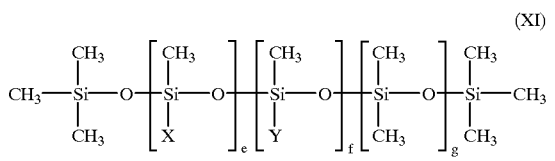

in which:
X denotes a group —$(CH_2)_3$—O—$(C_2H_4O—)_x$—$(C_3H_6O—)_y$—W, wherein W is a hydrogen atom, a C1–C16 alkyl, or a C1–C16 acyl;
Y is a C8–C22 alkyl or C8–C22 acyl radical,
g ranges from 0 to 200,
e ranges from 1 to 40,
f ranges from 1 to 100,
wherein the molecular weight of the residue —$(C_2H_4O—)_x$—$(C_3H_6O—)_y$—W preferably ranges from 250 to 2000, and x and y are selected such that the weight ratio of the oxyethylene groups/oxypropylene groups preferably ranges from 1000/0 to 20/80.

Silicone surfactants having an HLB which allows water-in-oil emulsions to be obtained are sold, for example, by the company Goldschmidt under the trade names ABIL WE 09, ABIL EM 90 and ABIL B8852, by the company Dow Corning under the names DC 3225 C, Q2-5220 and Q2-5200 and by the company Amerchol under the name SILSOFT BEAUTY AID SL.

Advantageously, a silicone surfactant of formula (XI) is used, and more preferably those for which W is a hydrogen atom and Y is a C8–C22 alkyl radical.

The surfactant used according to the invention can be present in the emulsion in a content preferably ranging from 5% to 12% by weight, and more preferably from 7 to 10% by weight, relative to the total weight of the emulsion.

The emulsion according to the invention also comprises, in a fatty phase, at least one volatile oil preferably in a content of at least 65% by weight relative to the total weight of the fatty phase.

In the present description, the term volatile oil is understood to refer to any oil which is able to evaporate on contact with the skin.

Preferably, oils whose flash point is sufficiently high to allow them to be used in formulation, and sufficiently low to obtain the desired evanescent effect, are used. Oils whose flash point is about 40–100° C. and/or whose vapor pressure, measured at 105 Pa and at 25° C., is greater than or equal to 0.02 mm Hg (2.6 Pa) and/or whose boiling point, measured at 105 Pa, is less than or equal to 275° C. are preferably used.

The volatile oil present in the fatty phase can be selected from hydrocarbon volatile oils and silicone volatile oils, and mixtures thereof.

Among the hydrocarbon volatile oils, mention may be made of isoparaffins and especially isododecane.

Among the volatile silicone oils, mention may be made of:
cyclic volatile silicones having from 3 to 8 and preferably from 4 to 6 silicon atoms. These are, for example, cyclotetradimethylsiloxane, cyclopentadimethylsiloxane or cyclohexadimethylsiloxane,
cyclocopolymers of the dimethylsiloxane/methylalkylsiloxane type, such as SILICONE FZ 3109 sold by the company Union Carbide, which is a dimethylsiloxane/methyloctylsiloxane cyclocopolymer, and
linear volatile silicones having from 2 to 9 silicon atoms. These are, for example, hexamethyl-disiloxane, hexylheptamethyltrisiloxane or octylheptamethyltrisiloxane.

The fatty phase of the emulsion according to the invention can comprise, in addition to the volatile oil, other non-volatile fatty substances usually used in the field of application envisaged. Preferably, the fatty phase comprises from 65% to 99% by weight, more preferably from 75% to 98%, relative to the total weight of the fatty phase, of silicone and/or hydrocarbon volatile oil, and preferably from 1% to 35%, more preferably from 2% to 25%, by weight of non-volatile fatty substances.

Among the non-volatile fatty substances, mention may be made of non-volatile oils, pasty fatty substances and plant, mineral, animal and/or synthetic gums and waxes, the latter comprising silicone fatty substances.

The pasty fatty compounds can be defined using at least one of the following physicochemical properties:
a viscosity preferably of from 0.1 to 40 Pa.s (1 to 400 poises), more preferably 0.5 to 25 Pa.s, measured at 40° C. with a Contraves TV rotary viscometer fitted with an MS-r3 or MS-r4 rotor operating at a frequency of 60 Hz,
a melting point preferably of 25–70° C., more preferably 25–55° C.

Among the silicone fatty substances, mention may be made of poly(C1–C20) alkylsiloxanes and phenylated silicone oils, as well as silicone gums and silicone waxes.

Among the non-silicone fatty substances, mention may be made of liquid paraffin, liquid petroleum jelly, perhydrosqualene, apricot oil, wheatgerm oil, sweet almond oil, beauty-leaf oil, palm oil, castor oil, avocado oil, jojoba oil, olive oil or cereal germ oil; fatty acid esters; alcohols; acetylglycerides; octanoates, decanoates or ricinoleates of alcohols or of polyalcohols; fatty acid triglycerides; glycerides; hydrogenated oils that are solid at 25° C.; lanolins; fatty esters that are solid at 25° C.; beeswax; plant waxes such as carnauba wax, candelilla wax, ouricurry wax, Japan wax, cork fibre wax or sugar cane wax; mineral waxes, for example paraffin wax, lignite wax or microcrystalline waxes or ozokerites; synthetic waxes, among which are polyethylene waxes and the waxes obtained by Fischer-Tropsch synthesis.

Preferably, the fatty phase comprises at least 75% by weight, relative to the total weight of the said fatty phase, of silicone and/or hydrocarbon volatile oil. More preferably, the fatty phase of the emulsion comprises 100% by weight, relative to the total weight of the fatty phase, of volatile oil.

The polyalkylsiloxanes according to the invention contain terminal trimethylsilyl groups. Those whose viscosity at 25° C. is less than or equal to 0.06 m2/s are preferably used and among which mention may be made of:

linear polydimethylsiloxanes and in particular those sold under the names "DOW CORNING FLUID 200" by the company Dow Corning alkylmethylpolysiloxanes such as cetyldimethicone (CTFA name).

The silicone gums can correspond to the formula:

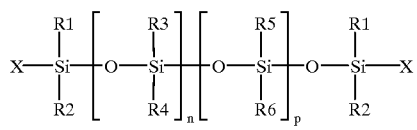

in which:

$R_1$, $R_2$, $R_5$ and $R_6$ are, together or separately, an alkyl radical having from 1 to 6 carbon atoms, $R_3$ and $R_4$ are, together or separately, an alkyl radical having from 1 to 6 carbon atoms or an aryl radical, and in particular phenyl, X independently denotes an alkyl radical having from 1 to 6 carbon atoms, a hydroxyl radical or a vinyl radical, n and p are selected so as to give the silicone gum a viscosity of greater than 100,000 mPa.s, preferably greater than 500,000 mPa.s.

Generally, n and p can denote values ranging from 0 to 5000, more preferably from 0 to 3000.

As silicone gums which can be used according to the invention, mention may be made of those for which:

the substituents $R_1$ to $R_6$ and X represent a methyl group, p=0 and n=2700, such as the one sold under the name SE30 by the company General Electric, the substituents $R_1$ to $R_6$ and X represent a methyl group, p=0 and n=2300, such as the one sold under the name AK 500,000 by the company Wacker, the substituents $R_1$ to $R_6$ represent a methyl group, the substituent X represents a hydroxyl group, p=0 and n=2700, as a 13% solution in cyclopentasiloxane, such as the one sold under the name Q2-1401 by the company Dow Corning, the substituents $R_1$ to $R_6$ represent a methyl group, the substituent X represents a hydroxyl group, p=0 and n=2700, as a 13% solution in polydimethyl-siloxane, such as the one sold under the name Q2-1403 by the company Dow Corning, the substituents $R_1$, $R_2$, $R_5$, $R_6$ and X represent a methyl-group and the substituents $R_3$ and $R_4$ represent a phenyl group, such that the molecular weight of the compound is 600,000 such as the one sold under the names "761" or "MIRASIL C-DPDM" by the company Rhône-Poulenc.

Preferably, silicone gums are used as other fatty substances.

These fatty substances can be selected in particular in a manner varied by a person skilled in the art in order to prepare a composition having the desired properties, for example in terms of consistency or texture. They are preferably used at a content of less than or equal to 7% by weight relative to the total weight of the emulsion, in order to retain the advantageous properties of the emulsion used according to the invention.

The aqueous phase of the emulsion according to the invention can comprise water or a flower water such as cornflower water.

In addition, the aqueous phase can comprise preferably from 0% to 14% by weight, relative to the total weight of the aqueous phase, of a lower C2–C6 monoalcohol and/or of a polyol such as glycerol, butylene glycol, isoprene glycol or propylene glycol.

In general, the emulsion according to the invention can comprise preferably from 30% to 55% by weight of fatty phase, from 5% to 12% by weight of surfactant and from 35% to 65% by weight of aqueous phase.

Moreover, the emulsion according to the invention can comprise preferably from 0 to 5% by weight, relative to the total weight of the emulsion, of at least one co-emulsifier which can be selected from fatty acid esters such as glyceryl stearate, acetylated ethylene glycol stearate, diglyceryl isostearyl succinate and sorbitan isostearate.

In addition, the emulsion according to the invention can comprise one or more thickeners in concentrations preferably ranging from 0 to 6% by weight, relative to the total weight of the emulsion.

The thickener can be selected from modified clays such as modified magnesium silicate (BENTONE GEL VS38 from Rheox) or hectorite modified with distearyidimethylammonium chloride (BENTONE 38 CE from Rheox).

The emulsion according to the invention can also comprise a particulate phase which can comprise pigments and/or pearlescent agents and/or fillers usually used in cosmetic compositions.

The pigments can be present in the emulsion in a proportion preferably ranging from 0–20% by weight, relative to the total weight of the emulsion, and more preferably in a proportion of 2–15%. They can be white or colored and inorganic and/or organic. Among the inorganic pigments, mention may be made of the titanium, zirconium or cerium dioxides, as well as the zinc, iron or chromium oxides, ferric blue, pearlescent agents such as mica coated with titanium oxide, with iron oxide, with natural pigment or with bismuth oxychloride, as well as colored titanium mica. Among the organic pigments, mention may be made of carbon black and the barium, strontium, calcium and aluminium lakes. The pigments can also have a hydrophobic surface or can be treated such as to make their surface hydrophobic; this treatment can be carried out according to the methods known to those skilled in the art; the pigments can especially be coated with silicone compounds such as PDMSs and/or with polymers, in particular polyethylene and/or amino acids.

The fillers, which can be present in the emulsion in a proportion preferably ranging from 0–20% by weight relative to the total weight of the emulsion, more preferably 0–10%, can be inorganic or synthetic and lamellar or non-lamellar. Mention may be made of talc, mica, silica, kaolin, TEFLON, starch, natural mother-of-pearl, boron nitride, microspheres such as EXPANCEL (Nobel Industrie) and POLYTRAP (Dow Corning). Preferably, spherical fillers less than 25 μm in size are used, such as polyethylene powders, Nylon powders, silicone resin microbeads (TOSPEARLS from Toshiba) and silica microspheres, it being possible for these fillers to contribute towards improving the transfer-free properties of the emulsions according to the invention.

The emulsion according to the invention can also comprise a cosmetically, pharmaceutically or hygienically acceptable medium. It can comprise, in this case, any additive usually used in the cosmetic, pharmaceutical or hygiene field, such as antioxidants, dyes, fragrances, essential oils, preserving agents, cosmetic active agents, moisturizers, vitamins, sphingolipids, liposoluble polymers and especially ones that are hydrocarbon, such as pblybutene, polyalkylenes, polyacrylates and silicone polymers which are compatible with fatty substances. Needless to say, a person skilled in the art will take care to select this or these optional additional compounds, and/or the amount thereof, such that the advantageous properties of the composition according to the invention are not, or are not substantially, adversely affected by the addition envisaged.

These additives can be present in the composition preferably in a proportion of 0–10% by weight.

The emulsions according to the invention can be in the form of a cosmetic product and especially in the form of a care product for the body and/or the face and/or the scalp, or alternatively in the form of a make-up product, in particular a foundation, a blusher, an eye shadow, an eye liner, a mascara or a lip composition.

The emulsions can also be in non-colored form, optionally containing cosmetic active agents. The emulsion according to the invention can be in the form of a cream, a milk or a serum, which is capable of being used as an antisun or care product.

The examples which follow serve to illustrate the invention without, however, being limiting in nature.

EXAMPLE 1

A water-in-oil emulsion having the following composition was prepared:

| Fatty phase: | |
|---|---|
| Mixture of polydiphenyldimethylsiloxane (MW = 600,000) and of cyclodimethylsiloxane (15/85) sold under the name MIRASIL C-DP DM by the company Rhône-Poulenc | 8 g |
| Co-emulsifier | 0.5 g |
| Cyclopentadimethylsiloxane | 14 g |
| Isododecane | 5 g |
| Pigments | 8 g |
| Nylon powder | 8 g |
| Thickener | 1.6 g |
| Aqueous phase: | |
| Aqueous dispersion of vinyl acetate/crotonic acid/vinyl 4-t-butylbenzoate copolymer (65/10/25) plasticized with diisopropyl adipate and having a solids content of 25% by weight (*) | 20 g |
| Diisopropyl adipate | 1 g |
| Mixture of cetyldimethicone copolyol, polyglycerolated isostearate (4 mol) and hexyl laurate, sold under the name ABIL WE 09 by the company Goldschmit | 9 g |
| Preserving agents | qs |
| Ethyl alcohol | 5 g |
| Demineralized water qs | 100 g |

(*) The polymer dispersion was prepared in accordance with Example 1 of European patent application EP-A-679,384, the disclosure of which is specifically incorporated by reference herein.

In order to prepare the emulsion, the emulsifier, the co-emulsifier and the thickener for the fatty phase were heated until homogeneous. Then, at 65° C., the silicone oils and the pigments were added, followed by the Nylon powder. The isododecane was then incorporated. Next, the aqueous phase was added and the emulsion was prepared with stirring using a standard turbomixer. Lastly, the ethanol was added and the mixture was homogenized.

A fine and uniform emulsion was thus obtained, which was stable on storage for at least 2 months at room temperature and at 45° C. The emulsion applied easily to the face, forming a uniform, supple and non-sticky film. It also had the advantage of not transferring onto a fabric applied to the skin.

We claim:

1. A composition comprising a water-in-oil emulsion comprising:

a fatty phase containing at least one volatile oil and at least one non-volatile fatty substance, wherein said non-volatile fatty substance is present in an amount not greater than 7% relative to the total weight of the emulsion, and an aqueous phase comprising at least one dispersed film-forming polymer, said polymer comprising at least one carboxylic acid monomer residue containing at least one ethylenic unsaturation and at least one carboxylic acid ester monomer residue wherein the group attached to the oxygen atom of said at least one carboxylic acid ester residue contains at least one ethylenic unsaturation.

2. A composition according to claim 1, wherein said composition is a cosmetic, pharmaceutical or hygiene composition.

3. A cosmetic, pharmaceutical or hygiene composition according to claim 2, wherein said composition is in the form of a make-up product or a care product.

4. A cosmetic, pharmaceutical or hygiene composition according to claim 3, wherein said make-up product is a foundation, a blusher, an eye shadow, an eye liner, a mascara or a lip composition.

5. A cosmetic, pharmaceutical or hygiene composition according to claim 3, wherein said care product is in the form of a cream, a milk, or a serum.

6. A cosmetic, pharmaceutical or hygiene composition according to claim 3, wherein said care product is an anti-sun product.

7. A non-therapeutic process for treating the skin or the scalp, said process comprising applying to said skin and/or said scalp an effective amount for said treatment of at least one composition comprising a water-in-oil emulsion, said emulsion comprising:

a fatty phase containing at least one volatile oil and at least one non-volatile fatty substance, wherein said non-volatile fatty substance is present in an amount not greater than 7% relative to the total weight of the emulsion, and an aqueous phase comprising at least one dispersed film-forming polymer, said polymer comprising at least one carboxylic acid monomer residue containing at least one ethylenic unsaturation and at least one carboxylic acid ester monomer residue wherein the group attached to the oxygen atom of said at least one carboxylic acid ester residue contains at least one ethylenic unsaturation.

8. A process for making up the skin and/or the scalp, said process comprising applying to said skin and/or said scalp an effective amount for said treatment of at least one composition according to claim 1.

9. A cosmetic, pharmaceutical or hygiene composition according to claim 2, wherein said composition is a transfer-free composition.

10. A process for decreasing the transfer and/or migration of a composition, said process comprising including in said composition a water-in-oil emulsion, said emulsion comprising:

a fatty phase containing at least one volatile oil and at least one non-volatile fatty substance, wherein said non-votatile fatty substance is present in an amount not greater than 7% relative to the total weight of the emulsion, and an aqueous phase comprising at least one dispersed film-forming polymer, said polymer comprising at least one carboxylic acid monomer residue containing at least one ethylenic unsaturation and at least one carboxylic acid ester monomer residue wherein the group attached to the oxygen atom of said at least one carboxylic acid ester residue contains at least one ethylenic unsaturation.

* * * * *